United States Patent [19]

Diatschenko et al.

[11] Patent Number: 5,353,627
[45] Date of Patent: Oct. 11, 1994

[54] PASSIVE ACOUSTIC DETECTION OF FLOW REGIME IN A MULTI-PHASE FLUID FLOW

[75] Inventors: Victor Diatschenko, Houston; Winthrop K. Brown, Bellaire; James R. Stoy, Missouri City, all of Tex.

[73] Assignee: Texaco Inc., White Plains, N.Y.

[21] Appl. No.: 109,064

[22] Filed: Aug. 19, 1993

[51] Int. Cl.$^5$ .............................. G01N 29/02
[52] U.S. Cl. ........................ 73/19.03; 73/61.45
[58] Field of Search .................... 73/19.03, 61.45

[56] References Cited

U.S. PATENT DOCUMENTS 4,926,675  5/1990  Schohl et al. ............... 73/19.03

FOREIGN PATENT DOCUMENTS 974248  11/1982  U.S.S.R. ..................... 73/19.03

Primary Examiner—Thomas P. Noland
Assistant Examiner—Joseph W. Roskos
Attorney, Agent, or Firm—James L. Bailey; Kenneth R. Priem; Russell J. Egan

[57] ABSTRACT

A method and apparatus for detecting the flow regime of multiphase fluid flowing in a closed pipeline system utilizes an entirely passive acoustical detector means. The acoustical pattern detected by the detector means is amplified and compared to known patterns to identify the flow regime according to its acoustical fingerprint.

10 Claims, 2 Drawing Sheets

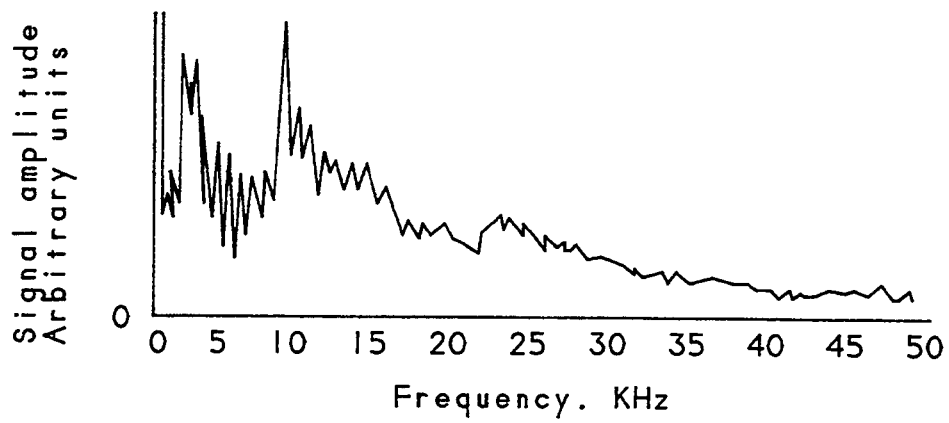
FIG. 2A SLUG FLOW
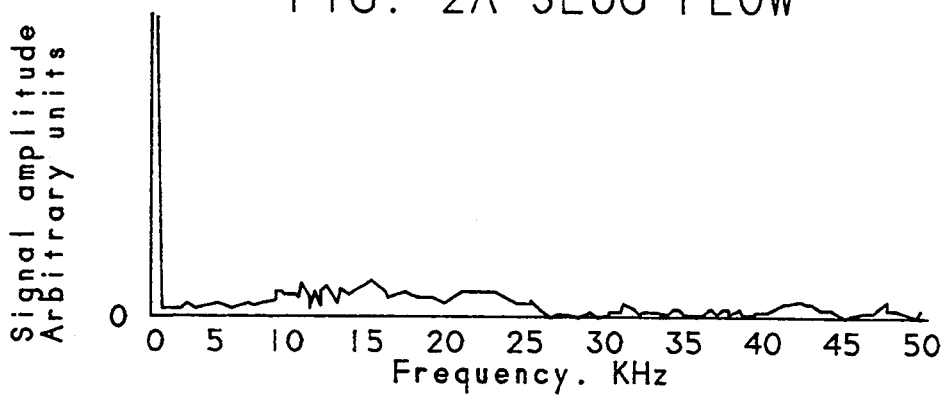
FIG. 2B STRATIFIED/WAVY
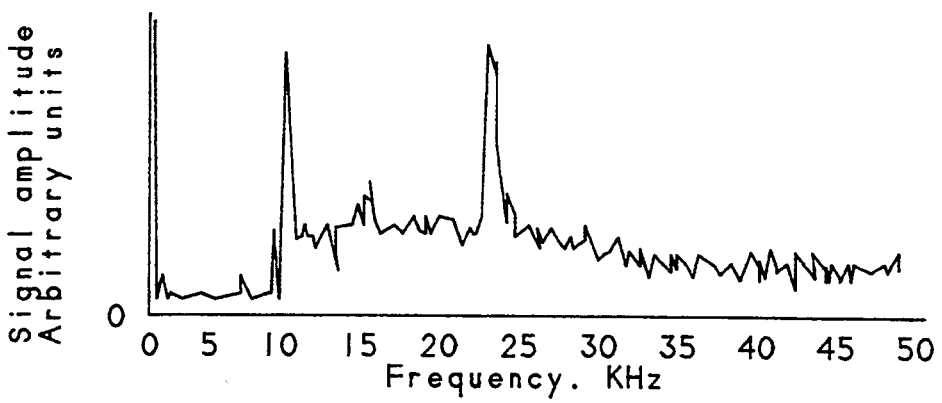
FIG. 2C ANNULAR
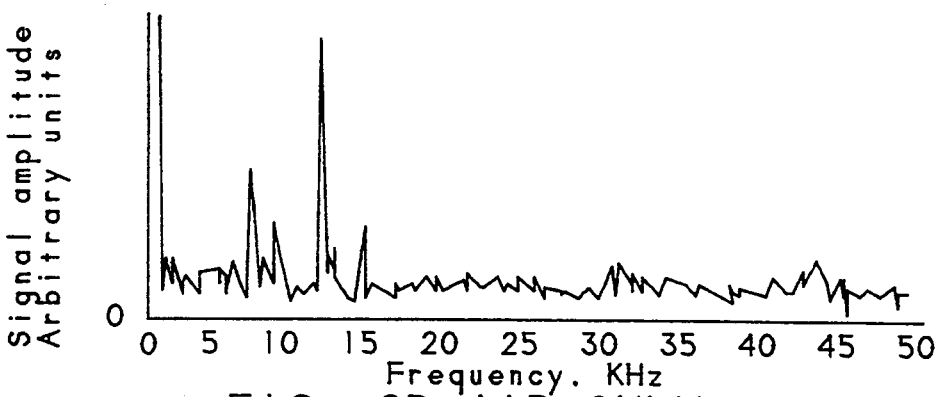
FIG. 2D AIR ONLY

5,353,627

PASSIVE ACOUSTIC DETECTION OF FLOW REGIME IN A MULTI-PHASE FLUID FLOW

BACKGROUND OF THE INVENTION

1. The Field of the Invention

The present invention relates to a method and apparatus to determine the flow regime of at least a two-phase fluid, such as a gas-liquid mixture, flowing through a pipe and, in particular, to a method and apparatus which are passive in nature, relying substantially entirely upon the acoustics created by the passage of the fluid mixture through the conduit.

2. The Prior Art

When two or more different fluids flow together as a mixture in a single conduit, the pattern of separation between the fluids (the flow regime) is determined by a number of factors including the relative mass ratio of one fluid to the other, the velocity of each fluid (the difference in velocity of one fluid with respect to another fluid is referred to as the "slip velocity"), the difference in viscosity between the fluids etc. It is to be understood that the general term "fluid" is here used to include gases, liquids, and solids in powder or pellet form. Flow regimes are generally categorized by terms which graphically describe the interface between the fluids in the mixture. At low velocity the mixture will generally separate into layers within the pipe, according to the density of the fluids, with the fluid of the greatest density occupying the lowest portion of the cross section of the pipe and the fluid of the least density occupying the uppermost portion of the pipe's cross section. When the interfaces between the fluids approximate horizontal planes, the fluid is characterized as a "stratified smooth flow". Increasing the velocity, or altering other factors of the mixture, can cause the interfaces between the fluids to become rippled in similar fashion to the surface of a body of water. Flow of mixtures with rippled, but distinct and density dominated interfaces between the fluids, is called "stratified wavy flow".

In gas-liquid systems with very low gas flow rates, a flow regime will develop such that the gasses are contained as discrete bubbles throughout the liquid. This is known as a "disbursed bubble flow". With higher gas flow rates, or different fluid properties, the bubbles can coalesce into long gas pockets which generally travel at the velocity of the liquid. This regime is called "elongated bubble flow". At high gas flow rates and low fluid flow rates, the gas may create waves on the surface of the liquid with enough height to cause the pipe to become bridged forming a liquid slug. The liquid slug then travels with a velocity equal to the velocity of the gas which created it. This regime is obviously known as "slug flow". At very high ratios of gas to liquid, the liquid may form an annular film in contact with the entire inner surface of the pipe, while the gas flows through the center of the pipe and liquid film causing a condition known as an "annular flow". Sometimes the gas flow within the annular liquid film contains small droplets of the entrained liquid to create the condition known as "annular mist flow". In general the flow regime observed in a given fluid flow system is a function of the relative contribution of the gravitational forces and viscous forces acting on the fluids individually and on the interface between the fluids.

There have been previous attempts made to monitor two-phase fluids flowing in pipes. An example is found in U.S. Pat. No. 4,193,290 in which a portion of the two-phase steam is bled through an orifice to an acoustical transducer which generates an output signal having an amplitude proportional to the quality of the steam being monitored.

U.S. Pat. No. 4,683,759 shows a device which employs gamma radiation transmission by one-shot collimation to determine the distribution of voids within a gas-liquid mixture. The distribution of voids in selective portions of the pipe, taken together with statistical and logical tests applied thereto, provide information from which are determined: the type of flow pattern or flow regime, the profile of a large gas bubble in slug flow, and the gas-liquid volume flow rates in slug flow.

U.S. Pat. No. 5,148,405 concerns a non-intrusive method for determining the characteristics of slug flow in multiphase flow pipelines by detecting acoustic emissions from the pipeline in the ultrasonic frequency range by means of at least one sound transducer. The output of the transducer is an analog electrical signal which is converted to a digital signal and analyzed to determine the characteristics of the slug flow.

It is also know that "sand-pipe" interaction, namely the movement of sand particles entrained in a fluid flowing in a pipe, generates acoustical noise in frequency ranges of 300 kHz to 800 kHz and which can be detected. These high frequencies are probably due to the very high flow velocities of fluids in pipes as described in "A Simple Clamp-on Sand Detector For Subsea Installation" by Asle Lygre, Trond Folkestad, Chr. Michelson Institute, Norway "Petroleum Abstracts #542,944".

SUMMARY OF THE INVENTION

The present invention relates to a method and apparatus which utilizes an entirely passive means to detect the flow regime of at least a two-phase fluid, such as a gas-liquid mixture, flowing through a pipe. At least one acoustic detection means is fixed to the pipe and generates a time dependent output signal. This signal is amplified and subjected to Fast Fourier Transformations with several transforms of the time varying wave form samples being averaged to generate a frequency-amplitude data set indicative of the type of flow regime.

BRIEF DESCRIPTION OF THE DRAWINGS

The present invention will now be described, by way of example, with reference to the accompanying drawings, in which:

FIG. 2 is a graph showing the acoustical signatures of four conditions within the pipe.

DETAILED DESCRIPTION OF THE PRESENT INVENTION

Figure 1:
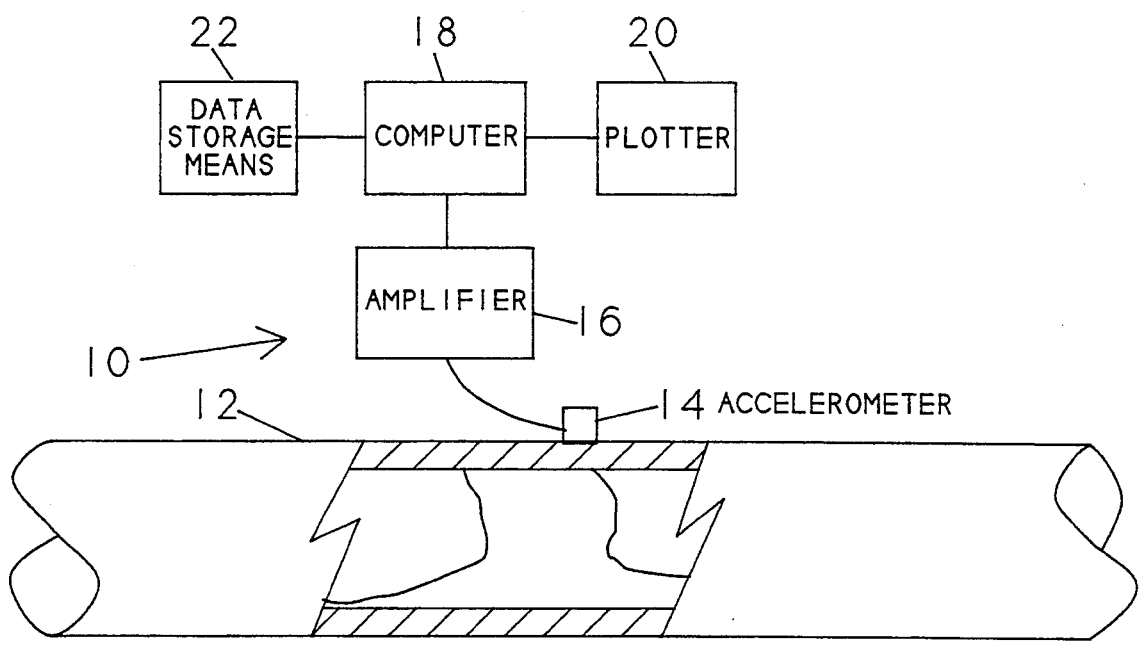
FIG. 1 is a schematic diagram of an apparatus according to the present invention for detecting the acoustical signatures of fluids flowing in a pipe.

Knowledge of the type of flow regime which exists in pipe is important to the operators of multiphase fluid pipelines for a number of reasons. For example, certain types of flow measurement systems require that a particular flow regime exists in order to obtain an accurate measurement of the fluid flow. Also the magnitude of pressure losses due to fluid friction in the pipe are dependent upon the flow regime. Further, slug flow within the pipe can cause intermittent vibration and/or shock within the pipe. These shocks are transmitted to the pipe's supporting structures and can cause damage to the supports or to the pipe itself possibly resulting in leaks, ruptures and injury to personnel in the vicinity of the damage. Some flow regimes promote separation of the fluid phases at piping junctions causing unequal distribution of the fluids through the junction.

The present invention concerns a method and apparatus for determining the flow regime of a multiphase fluid flowing in a pipe. No other known system, device or procedure attempts to detect the flow regime of a multi-phase fluid flowing through a pipe in the manner of the present invention. The present invention is non-nuclear, does not require the physical penetration of the pipe wall, nd does not require the generation of an excitation signal. Instead it is completely passive relying entirely upon the acoustics generated by the movement of a multi-phase fluid in the pipe. The acoustic phenomena exploited by this invention occur naturally in the flow of multi-phase fluid mixtures. Thus the invention functions in an entirely passive mode obviating any requirement for excitation means in order to properly determine to flow regime.

It is common knowledge that the flow of fluids through a pipe causes noise to be created within the pipe. The present invention deals with a method and apparatus by which this noise is recorded and analyzed such that a fingerprint of the noise is created. Each of the flow regimes described above generates noise with a characteristic fingerprint (actually a plot of amplitudes of the vibrations versus the frequencies at which the vibrations occur). By obtaining a plot of frequency versus amplitude from the noise outside a given pipe, through which a mixture of fluids flow, the regime in which the mixture flows can be determined.

FIG. 1 is a schematic diagram of an apparatus through which a mixture of air and water flows under pressure. The invention 10 is shown in connection with a straight horizontal section of pipe 12. Attached to the outer surface of the pipe is at least one piezoelectric accelerometer 14. Each of the at least one accelerometers is capable of converting vibrations detected in the pipe wall into electrical signals. Each accelerometer 14 is connected to its own amplifier 16. The time dependent output from each amplifier 16 is fed through its respective amplifier to and sampled by a frequency analyst computer 18, which performs a Fast Fourier Transformation on the time varying wave form samples. Several Fast Fourier Transformed samples are averaged to generate a frequency amplitude data set which is conveniently plotted, with amplitude on the vertical axis and vibrational frequency on the horizontal axis, in a plotter 20. This information is also stored in a data storage means 22.

Turning now to FIG. 2, four plots are shown, each of which depicts the acoustic spectrum or fingerprint of a distinctive flow regime. The acoustic spectrum of slug flow (the uppermost plot) is characterized by the relative magnitude of the vibrations in the 0 to 6 kHz range and by the attenuated vibrations in the 20 to 25 kHz range. Stratified wavy flow is characterized by the generally very low amplitude of vibrations in a wide range of frequencies. Annular flow is characterized by the distinct high amplitude vibrations in the 22 to 25 kHz range and by the attenuation of the vibrations in the 0 to 10 kHz range. It is interesting to note that the slug and annular flow regimes tend to exhibit somewhat opposite frequency spectra; frequency ranges active in slug flow are attenuated in annular flow and the frequency ranges active in the annular flow are attenuated in the slug flow. This is significant in that most industrial gas-liquid flowing systems operate in either the slug or annular flow conditions. A frequency spectrum for air only (single-phase gas flow) is included for a baseline reference. The air only spectrum indicates only measurable vibrations throughout the frequency range investigated with the only significant amplitude peaks occurring in the 7 to 15 kHz range, a range in which all flow regimes exhibit amplitude peaks.

The operation of the present invention has been verified by using a transparent pipe section to visually observe the various flow regimes as they were acoustically detected. These experiments also prove that the material of the pipe (namely, plastic or metal) was not a factor in making a correct determination. It was also further learned that the number and positioning of the accelerometers is not a factor in correctly determining the flow regime. The present invention has been described with reference to a horizontal section of pipe. While this is probably the most likely and convenient configuration for the pipe, the invention is not so limited.

The above described embodiment of the present invention has been in reference to a gas-liquid combination. There is no reason why the present invention could not be applied to any flow regime, such as a solid-gas fluid flow, in order to monitor the flow of powder or pellet materials within a pipe. In fact, the noise generated by such regimes may be more easily detected.

The present invention may be subject to many modifications and changes which would be apparent to those skilled in the art. The present embodiment is to be considered in all respects as being illustrative and not restrictive of the scope of the invention as defined by the appended claims.

We claim:

1. A method for determining the flow regime of a multiphase fluid flowing in a pipe comprising the steps of:
   providing at least one acoustical detection means in physical contact with a pipe surface;
   providing means to receive and amplify signals generated by said acoustical detection means;
   providing means to receive and analyze said amplified signals originating from said acoustical detection means;
   taking a continuous series of acoustical signals from said acoustical detection means and generating a corresponding series of time dependent wave form signals; and
   analyzing said time dependent wave form signals by comparison with known fingerprints of various flow regimes whereby the current flow regime of multiphase fluid is determined.

2. A method according to claim 1 wherein said analyzing comprises:
   performing Fast Fourier Transformations on said time varying wave form samples; and
   averaging several Fast Fourier Transformed samples to generate a frequency amplitude data set which can be conveniently plotted.

3. The method according to claim 1 wherein relative magnitude of vibrations in the 0 to 6 kHz range and attenuated vibrations in the 20 to 25 kHz range is indicative of slug flow.

4. The method according to claim 1 wherein a very low amplitude of vibrations in a wide range of frequencies is indicative of stratified wavy flow.

5. The method according to claim 1 wherein amplitude vibrations in the 22 to 25 kHz range and attenuation of vibrations in the 0 to 10 kHz range is indicative of annular flow.

6. An apparatus for determining the flow regime of multiphase fluid flowing through a pipe comprising:
- at least one acoustic detection means in physical contact with a pipe surface and capable of generating electrical signals in response to detection of acoustic noise;
- means connected to said acoustical detection means to amplify said signals generated thereby; and
- means to receive and analyze said amplified signals and display the results whereby the flow regime is identified from its characteristic frequency pattern.

7. An apparatus according to claim 6 wherein said signals are time varying wave form signals and said means to receive and analyze said signals comprises:
- means to perform a Fast Fourier Transformation on said signals; and
- means to average several of said Fast Fourier Transformed signals to generate a frequency amplitude data set which can be convieniently plotted.

8. An apparatus according to claim 6 wherein said acoustic detection means is a piezoelectric accelerometer.

9. An apparatus according to claim 6 wherein each said at least one acoustic detection means generates a time dependent output signal.

10. An apparatus according to claim 6 wherein said means to analyze and display said signals comprises:
- a frequency analyst computer.

* * * * *